US008622890B1

(12) United States Patent
Caggiano et al.

(10) Patent No.: US 8,622,890 B1
(45) Date of Patent: Jan. 7, 2014

(54) FLEXIBLE MULTI-CONFIGURATION FEMALE SEXUAL STIMULATION DEVICE

(75) Inventors: Keith Caggiano, Playa del Rey, CA (US); Justin Ross, Beverly Hills, CA (US)

(73) Assignee: Momentum Management, LLC, Torrance, CA (US)

( * ) Notice: Subject to any disclaimer, the term of this patent is extended or adjusted under 35 U.S.C. 154(b) by 586 days.

(21) Appl. No.: 12/928,734

(22) Filed: Dec. 17, 2010

(51) Int. Cl.
*A61F 5/00* (2006.01)

(52) U.S. Cl.
USPC .......... 600/38

(58) Field of Classification Search
USPC .......... 600/38–41; 601/46, 80, 81, 84
See application file for complete search history.

(56) References Cited

U.S. PATENT DOCUMENTS

| | | | | |
|---|---|---|---|---|
| 7,166,072 | B2 * | 1/2007 | Smith | 600/38 |
| 2005/0273024 | A1 * | 12/2005 | Nan | 601/71 |
| 2010/0174135 | A1 * | 7/2010 | Shim | 600/38 |
| 2011/0034763 | A1 * | 2/2011 | Domnick et al. | 600/38 |
| 2012/0330201 | A1 * | 12/2012 | Turner et al. | 601/46 |
| 2013/0109913 | A1 * | 5/2013 | Imboden et al. | 600/38 |

FOREIGN PATENT DOCUMENTS

| | | |
|---|---|---|
| CA | 2471515 | 9/2003 |
| EP | 1 477 149 A1 | 11/2004 |
| GB | 2401551 B | 11/2006 |

* cited by examiner

*Primary Examiner* — John Lacyk
(74) *Attorney, Agent, or Firm* — Thomas I. Rozsa

(57) ABSTRACT

The present invention is a female sexual stimulation device to aid in arousal of a female through labial, clitoral, penetrative and "G" spot stimulation The device is flexible and can be formed into any desired multiplicity of shapes such as straight, a question mark, and angular so that the female sexual organ can be penetrated and aroused in different areas. The device includes protrusions to aid in stimulation and also includes a vibrator to further aid in stimulation.

18 Claims, 10 Drawing Sheets

FLEXIBLE MULTI-CONFIGURATION FEMALE SEXUAL STIMULATION DEVICE

BACKGROUND OF THE INVENTION

1. Field of the Invention

The present invention relates to the field of sex toys and in particular, to sex toys which are used to stimulate the female sexual organs either during masturbation or sexual intercourse. The present invention relates to the field of sex toys used for labial, clitoral, penetrative and"G" spot stimulation.

2. Description of the Prior Art

In general, sex toys are known in the prior art. One example of a sex toy used for giving labial, clitoral, penetrative and "G" spot stimulation to a female is set forth in UK Patent GB 2 401 551 B and its corresponding European Patent No. EP 1 477 149 A1 and Canadian Patent CA 2412525. In this device, there is disclosed a female stimulation aid comprising a first handle portion and a second penetrative shaft portion connected together at their respective proximal ends to form a generally U-shaped stimulation device which is fairly rigid and thick in configuration and requires firm gripping of a handle portion to facilitate penetration of the device at a curved hook end into a female. The device also has an inner face with transverse ribs to provide additional stimulation. Although the patent talks in general about other variations, there is only illustrated and discussed in detail the single, fairly rigid and thick U-shaped curved device.

There is a significant need for an improved sex toy which provides numerous other alternative features to aid in female sexual stimulation.

SUMMARY OF THE INVENTION

The present invention is a female sexual stimulation device to aid in arousal of a female through labial, clitoral, penetrative and "G" spot stimulation The device is flexible and can be formed into any desired multiplicity of shapes such as straight, a question mark, and angular so that the female sexual organ can be penetrated and aroused in different areas. The device includes protrusions to aid in stimulation and also includes a vibrator to further aid in stimulation.

It is an object of the present invention to provide a flexible multi-configuration female sexual stimulation device to aid female masturbation and pre-intercourse stimulation by enabling a user to provide labial, clitoral, penetrative and "G" spot stimulation in various manners due to the fact that the device is flexible and can be configured into any multiplicity of desired shapes.

It is a further object of the present invention to provide a female sexual stimulation aid which contains a multiplicity of differently shaped protrusions which can stimulate different portions of a female sexual organ as the device is caused to vibrate through an interior vibrator which causes a copper wire to transmit the vibration throughout the entire device.

It is another object of the present invention to provide a female sexual stimulation aid which includes a lubricant reservoir on its exterior surface to retain lubricant for a prolonged period of time to enable utilization of the device for several minutes without having to replenish lubricant.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Figure 1:
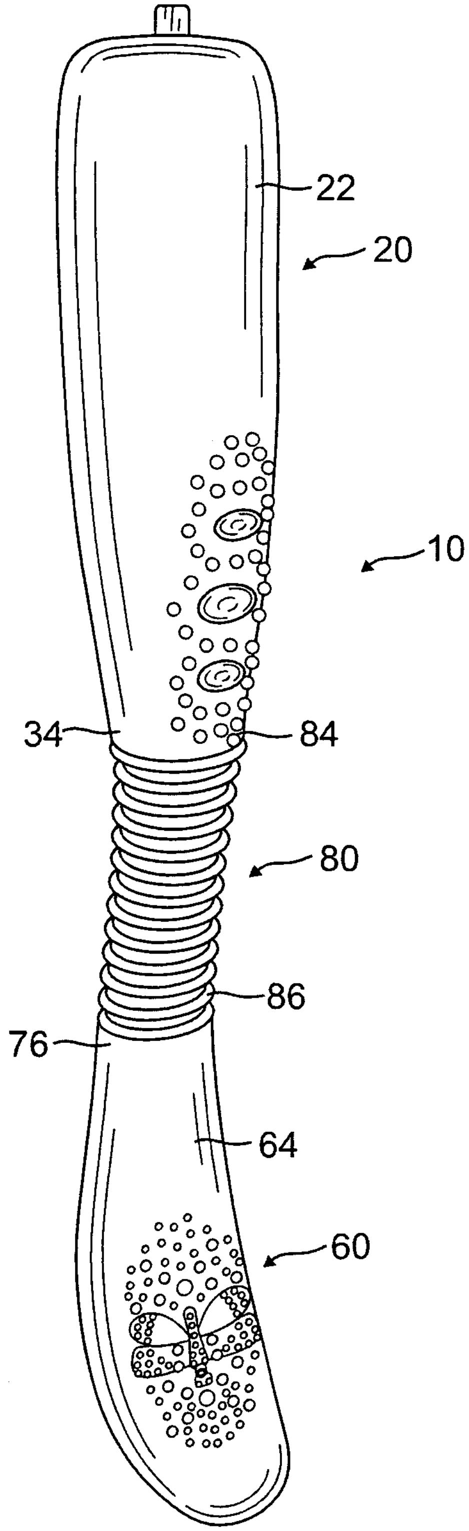
FIG. 1 is a perspective view of the present invention flexible multi-configuration female sexual stimulation device, illustrated in an elongated configuration.
Figure 2:
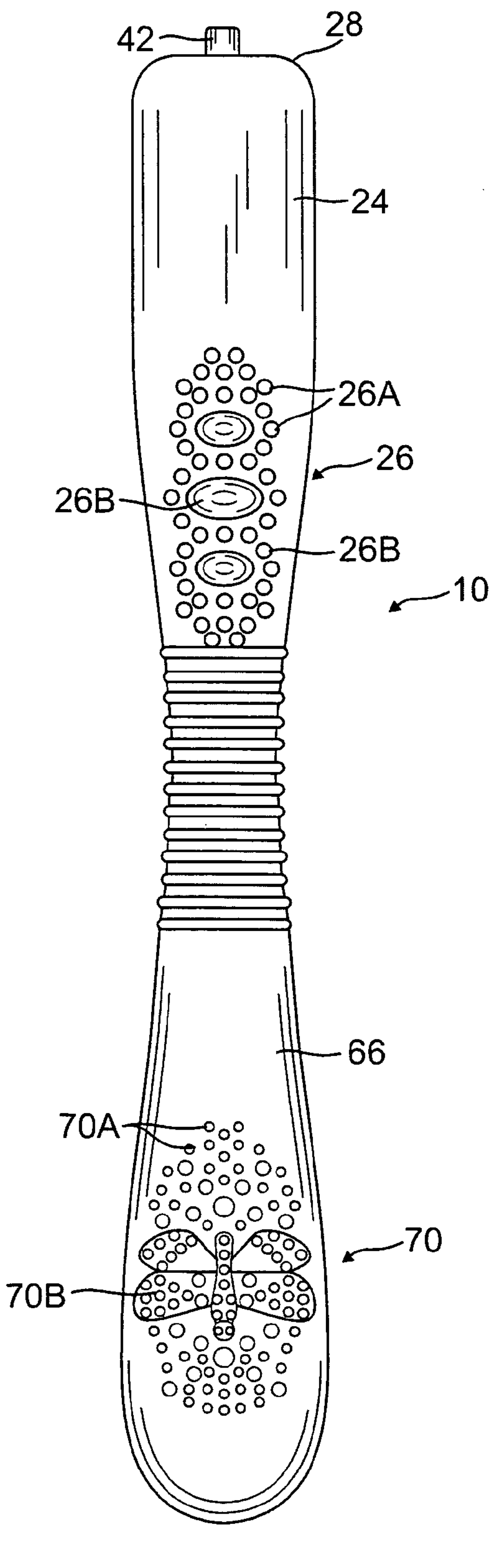
FIG. 2 is a front elevational view of the flexible multi-configuration female sexual stimulation device, illustrated in an elongated configuration.
Figure 3:
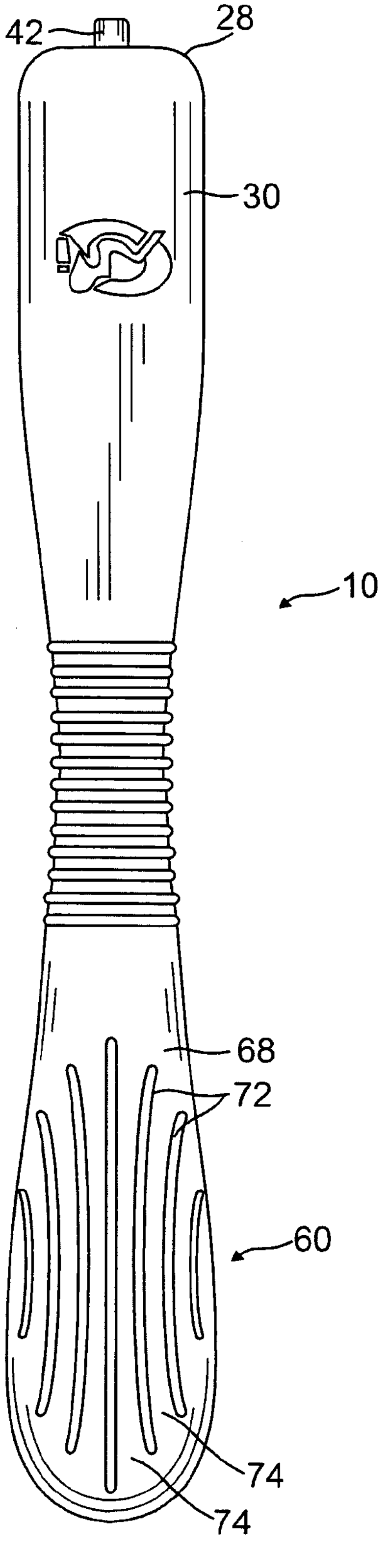
FIG. 3 is a rear elevational view of the flexible multi-configuration female sexual stimulation device, illustrated in an elongated configuration.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1 through 8, there are illustrated perspective, front, rear, right side, left side, top, bottom and cross-sectional views of the present invention flexible multi-configuration sexual stimulation device 10. The device 10 has a first section 20 and a flexible second section 60 interconnected by a flexible interconnecting section 80. Although described in three sections, the device 10 is one integral unit formed out of flexible material selected from the group consisting of soft rubber and silicone. The first section has an exterior surface 22 having an interior face 24 and an exterior face 30. The interior face 24 has a multiplicity of stimulation mechanisms 26 protruding from the interior face 24. The stimulation mechanisms include a multiplicity of randomly spaced generally round bumps 26A and a multiplicity of generally oval spaced protrusions 26B interspersed within the multiplicity of generally round bumps 26A. It will be appreciated that the shapes of the stimulation mechanisms can be any desired shape in addition to round and oval, including but not limited to square, rectangular, ellipsoidal, pentagonal, hexagonal, and octagonal. While illustrated as located adjacent to the flexible interconnecting section 80, it will be appreciated that the stimulation mechanisms 26 can be positioned at any desired location or locations on the interior face 24 of exterior surface 22.

Figure 8:
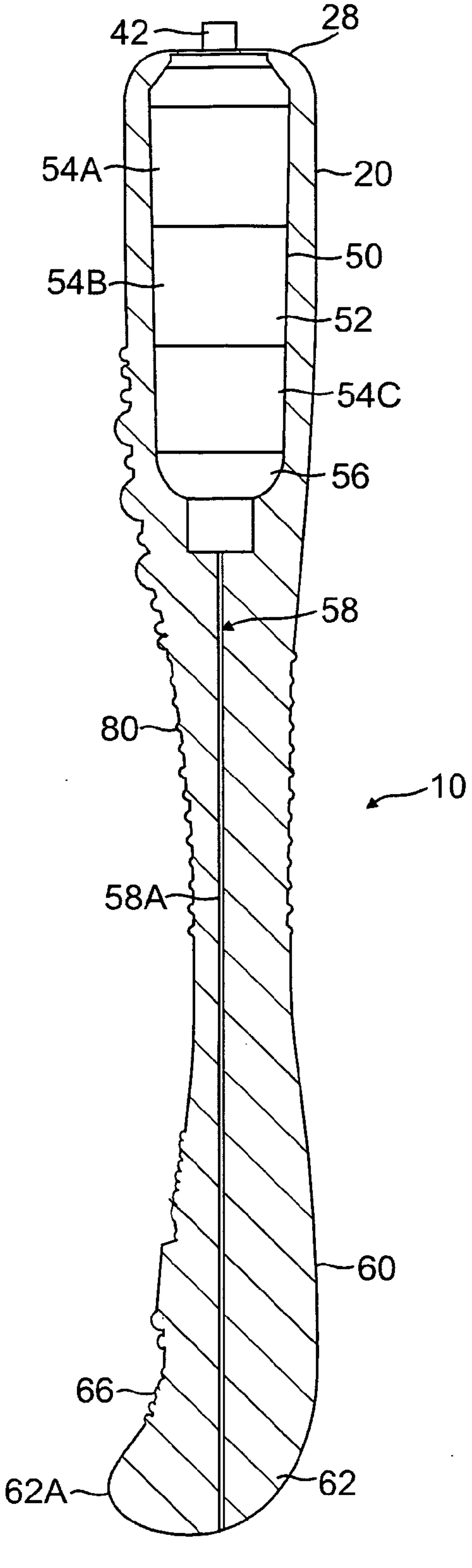
FIG. 8 is an elongated cross-sectional view of the flexible multi-configuration female sexual stimulation device, taken along line 8-8 of FIG. 4.
Figure 9:
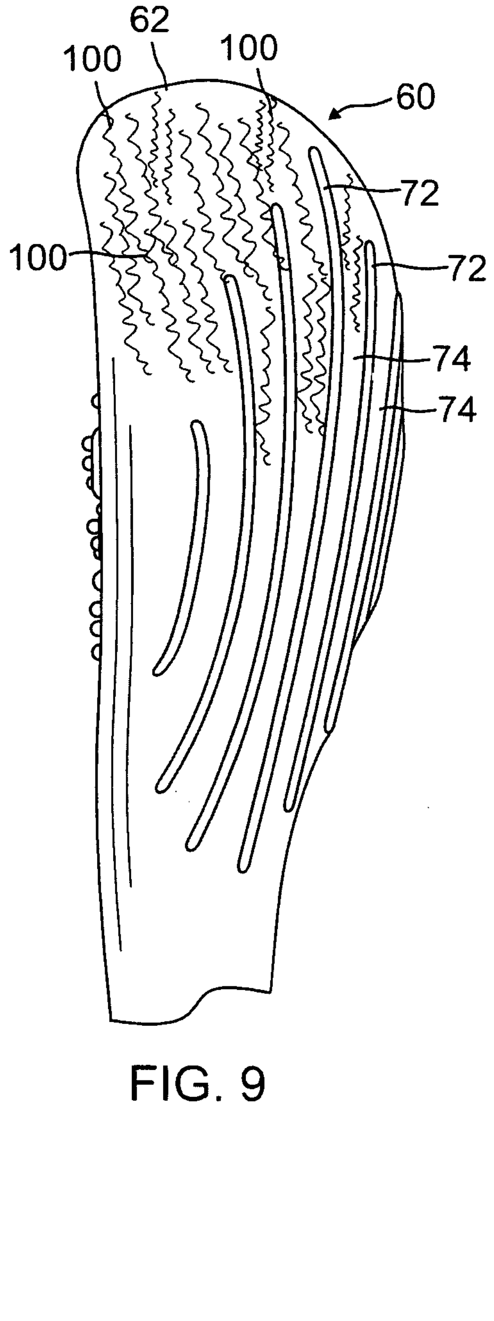
FIG. 9 is an enlarged perspective view of the lower rear surface of the flexible multi-configuration female sexual stimulation device, illustrating the lubricant retaining channels thereon.

The first section 20 of device 10 is intended to be used as a handle by which the device can be grasped. The first section 20 is retained in the palm of one hand and encircled by at least some of the fingers of the hand. An activation mechanism 42 such as a push button extends out of the top surface 40 adjacent a distal end 28 of the first section 20 of device 10. Referring to FIG. 8, the device 10 includes an interior chamber 50 within first section 20, the chamber retaining a power supply 52 which can be one or a multiplicity of batteries 54A, 54B and 54C. The power supply 52 is in electrical communication with a vibrator 56 which in turn is connected to a vibration transmitting mechanism 58 which, by way of example, can be a copper wire 58A extending from the vibrator 56 through the interior of the device 10, extending through the flexible interconnecting section 80 and into the second section 60 and terminating adjacent the distal end 62 of flexible second section 60. When the activation mechanism 42 is activated such as pushing down on the push button, the vibrator 56 is activated causing the vibration mechanism 58 to vibrate within the device 10, thereby causing the first section 20, interconnecting section 80 and second section 60 to vibrate. The vibration will continue until the activation mechanism 42 is once against activated such as pushing on the pushbutton to turn off the vibrator 56. Alternatively, to save battery life, the period of time of activation of the vibrator 56 can be preset after activation such as one minute, two minutes, etc., and the vibrator 56 will automatically turn off after the preset period of time.

Figure 4:
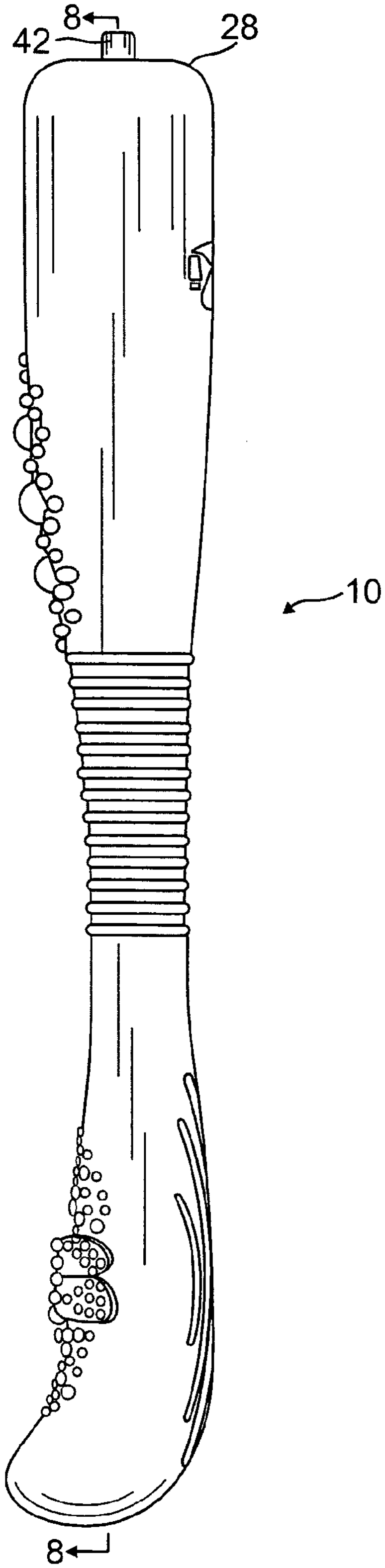
FIG. 4 is a side elevational view when viewed from the right side of the flexible multi-configuration female sexual stimulation device, illustrated in an elongated configuration.
Figure 5:
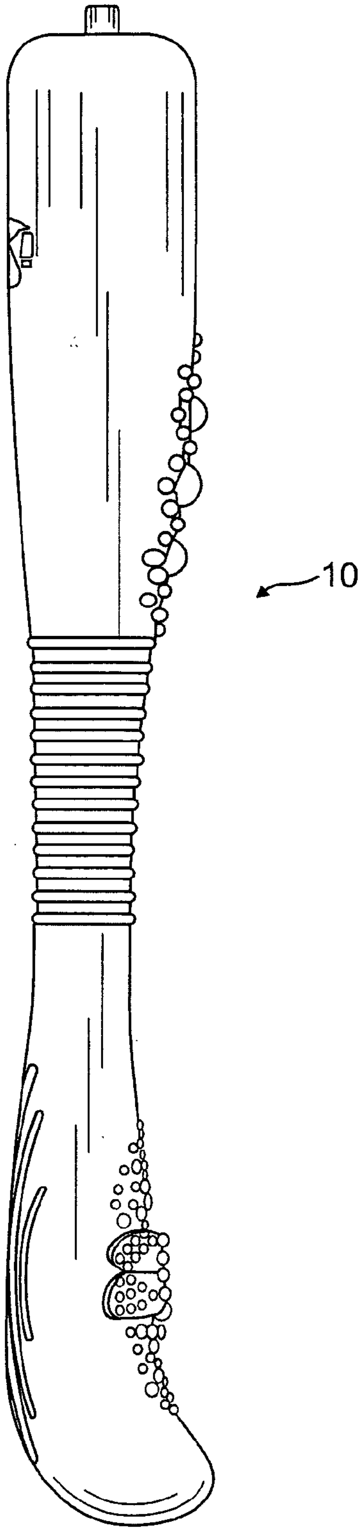
FIG. 5 is a side elevational view when viewed from the left side of the flexible multi-configuration female sexual stimulation device, illustrated in an elongated configuration.
Figure 6:
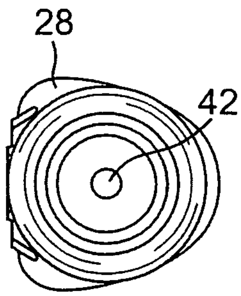
FIG. 6 is a top plan view of the flexible multi-configuration female sexual stimulation device.
Figure 7:
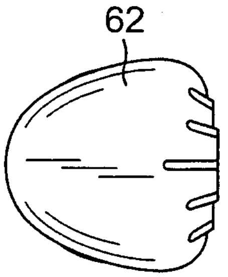
FIG. 7 is a bottom plan view of the flexible multi-configuration female sexual stimulation device.

The flexible second section 60 has an exterior surface 64 having an interior face 66 and an exterior face 68. The interior face 66 has a multiplicity of stimulation mechanisms 70 protruding from the interior face 66. The stimulation mechanism includes a multiplicity of randomly spaced generally round bumps 70A and a decorative design 70B which as illustrated is a butterfly. It will be appreciated that the stimulation mechanism 70 can be of any shape and of any decorative design. As best illustrated in FIGS. 4, 5 and 8, the distal end 62 of second section 60 is rounded and extends in an arcuate manner relative to interior face 66, projecting away from interior face 66 and having an interior rounded tip 62A.

A key innovation of the present invention is the inclusion of a multiplicity of longitudinally projecting protrusions 72 extending away from exterior face 68 of second section 60. The longitudinally projecting protrusions 72 are separated by longitudinal spaces 74. The longitudinal protrusions 72 act as lubricant retaining barriers for lubricant 100 which is retained in the spaces 74 between the longitudinally projecting protrusions 72. The longitudinal protrusions 72 and spaces 74 form a lubricant reservoir. As a result, lubricant 100 applied to the exterior face 68 of the second section 60 is retained in the lubricant retaining barriers formed of the longitudinally extending protrusions 72 and spaces 74 therebetween so that the device can be used for several minutes without having to replenish lubricant 100.

Figure 10:
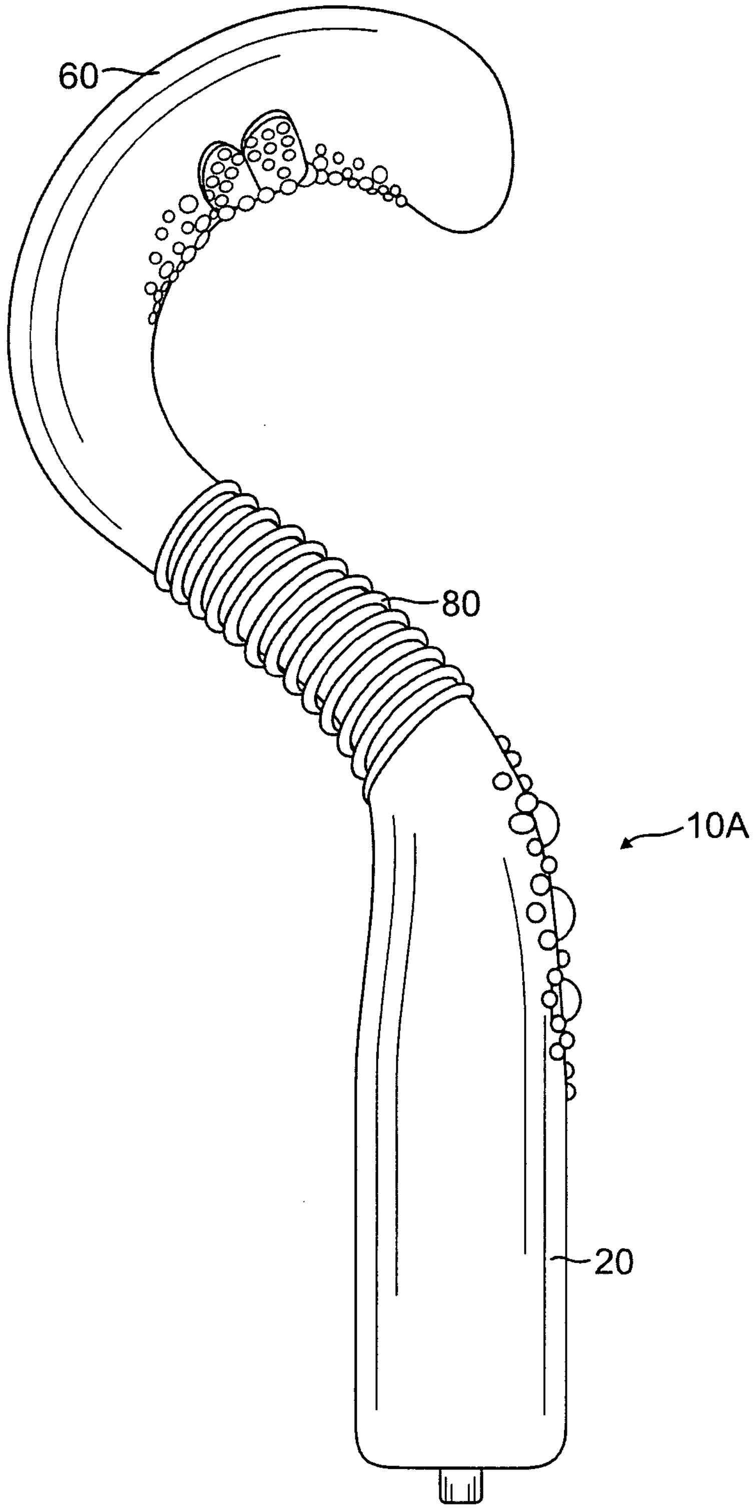
FIG. 10 is a perspective view of the present invention flexible multi-configuration female sexual stimulation device, illustrated in a question mark configuration.
Figure 11:
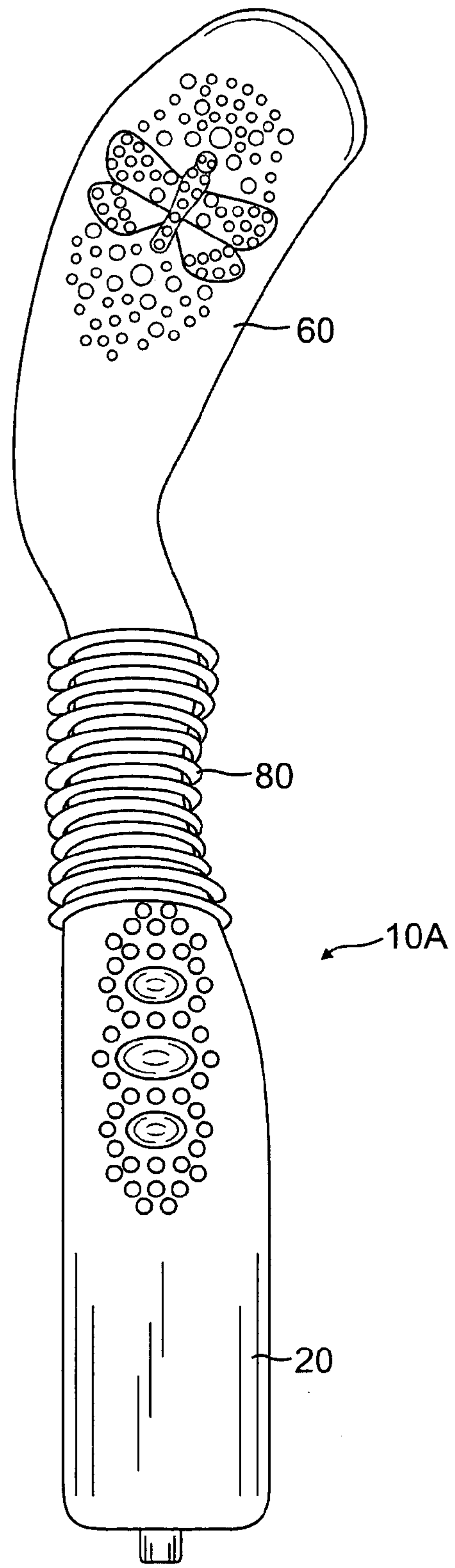
FIG. 11 is a perspective view of the present invention flexible multi-configuration female sexual stimulation device, illustrated in one alternative variation of a twisted configuration.

Another unique feature of the present invention device 10 is the incorporation of the flexible interconnecting section 80 having a first end 84 which is adjoined to proximal end 34 of the first section 20 and a second end 86 which is adjoined to proximal end 76 of second section 60. The flexible interconnecting section 80 enables the device 10 to be twisted, contorted and bent into any desired multiplicity of shapes. By way of example, the device can be twisted into the shape of a question mark 10A as illustrated in FIG. 10, where the first section 20 is the stem of the question mark and is grasped in one hand, the interconnecting section 80 is the center of the question mark and the second flexible section 60 is the arcuate part of the question mark. The second section 60 is also flexible so that it can be formed into any desired configuration. The device 10B can also be contorted into numerous twisted configurations as illustrated in FIG. 11. In the alternative configuration illustrated in FIG. 11, the second section 60 is twisted to be at an angle to the interconnecting section 80 and first section 20. It will be appreciated that the device 10 can be twisted into any configuration to accommodate the wishes of the user. The flexibility of the interconnecting section 80 and flexibly of the second section 60 enables the device 10 to be twisted into any desired varied shape to accommodate the pleasure of the user.

In operation, a user grasps the first section 20 so that it rests in the palm of one hand and at least several fingers encircle the first section 20. The second section 60 penetrates the female sexual organ and the stimulation mechanism such as 70A and 70B stimulate the user's labia and clitoris. The vibrator 56 is also activated to provide further stimulation. The device 10 can be configured into different shapes to enhance sexual pleasure. Lubricant 100 is preferably applied to the lubricant reservoir 72 before use to enhance and lengthen the sexual stimulation.

Through further penetration, the user's vaginal entrance and internal vaginal walls are stimulated by the protrusions 70 on the second section 60, and the protrusions 26 on the first section 20 and the vibrator 56 is activated for further stimulation. The rounded tip 62A at the distal end 62 of the second section 60 is used to stimulate the "G" spot.

The ability to configure the device into any multiplicity of desired shapes facilitates accommodating different women who have sexual organs of different shapes and sizes.

The device 10 is preferably made of soft rubber and silicone due to its ability to transmit vibration and stimulation and can also be easily cleaned after use.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A female sexual stimulation device, comprising:

a. a first section, a flexible second section, a flexible interconnecting section all formed in one piece, a proximal end of the first section adjoining a first end of the interconnecting section and a proximal end of the flexible second section adjoining a second end of the interconnecting section;

b. the first section having an exterior surface having an interior face and an exterior face, the interior face having a multiplicity of stimulation mechanisms protruding from the interior face, the first section configured to be grasped by a hand;

c. an activation mechanism extending out of a top surface adjacent a distal end of the first section, the first section including an interior chamber retaining a power supply in electrical communication with a vibrator which in turn is connected to a vibration transmitting mechanism extending from the vibrator through the interior of the device and extending through the flexible interconnecting section and into the flexible second section and terminating adjacent a distal end of the second section so that when the activation mechanism is activated, the vibrator is activated and causes the vibration mechanism to vibrate within the device, thereby causing the first section, the interconnecting section and second section to vibrate;

d. the flexible second section having an exterior surface having an interior face and an exterior face, the interior face having a multiplicity of stimulation mechanisms protruding from the interior face, the distal end of the second section is rounded and extends in an arcuate manner relative to the interior face projecting away from the interior face and having an interior rounded tip, a multiplicity of longitudinally projecting protrusions extending away from the exterior face of the flexible second section, the longitudinally projecting protrusions are separated by longitudinal spaces, the longitudinal projecting protrusions acting as lubricant retaining barriers for lubricant retained in the spaces between the longitudinally projecting protrusions; and e. the flexible interconnecting section and flexible second section enable the device to be configured, twisted and contorted into any desired multiplicity of shapes.

2. The female sexual simulation device in accordance with claim 1, further comprising: the stimulation mechanisms on the front face of the first section are selected from the group consisting of a multiplicity of randomly spaced generally round bumps, a multiplicity of generally oval spaced protrusions interspersed within the multiplicity of generally round bumps, and protrusions which are square, rectangular, ellipsoidal, pentagonal, hexagonal and octagonal.

3. The female sexual stimulation device in accordance with claim 1, further comprising: the stimulation mechanisms on the front face of the first section are adjacent to the interconnecting section.

4. The female sexual stimulation device in accordance with claim 1, further comprising: the vibration transmitting mechanism is copper wire.

5. The female sexual simulation device in accordance with claim 1, further comprising: the stimulation mechanisms on the front face of the flexible second section are selected from the group consisting of a multiplicity of randomly spaced generally round bumps and a decorative design.

6. The female sexual stimulation device in accordance with claim 1, further comprising: the power supply is at least one battery.

7. The female sexual stimulation device in accordance with claim 1, further comprising the device can be contorted, twisted and bent to form a shape selected from the group consisting of generally tubular shaped, a question mark and an angular shape where the flexible second section is at any desired angle relative to the interconnecting section.

8. The female sexual stimulation device in accordance with claim 1, further comprising: the first section, flexible interconnecting section, and flexible second section are made out of material selected from the group consisting of: soft rubber and silicone.

9. A female sexual stimulation device, comprising:

a. a first section, a second section, a flexible interconnecting section all formed in piece, a proximal end of the first section adjoining a first end of the interconnecting section and a proximal end of the second section adjoining a second end of the flexible interconnecting section;

b. the first section having an exterior surface having an interior face, the interior face having a multiplicity of stimulation mechanisms protruding from the interior face, the first section configured to be grasped by a hand;

c. an activation mechanism retained with the first section, the first section including an interior chamber retaining a power supply in electrical communication with a vibrator which in turn is connected to a vibration transmitting mechanism extending from the vibrator through the interior of the device and extending through the flexible interconnecting section and into the second section and terminating adjacent a distal end of the second section so that when the activation mechanism is activated, the vibrator is activated and causes the vibration transmitting mechanism to vibrate within the device, thereby causing at least the second section to vibrate;

d. the second section having an exterior surface having an interior face and an exterior face, the interior face having a multiplicity of stimulation mechanisms protruding from the interior face, the distal end of the second section is rounded and extends in an arcuate manner relative to interior face projecting away from interior face and having an interior rounded tip, a lubricant reservoir incorporate into the exterior face; and e. the flexible interconnecting section and second section enable the device to be configured, twisted and bent into any desired multiplicity of shapes.

10. The female sexual simulation device in accordance with claim 9, further comprising: the stimulation mechanisms on the front face of the first section are selected from the group consisting of a multiplicity of randomly spaced generally round bumps, a multiplicity of generally oval spaced protrusions interspersed within the multiplicity of generally round bumps, and protrusions which are selected to the group consisting of square, rectangular, ellipsoidal, pentagonal, hexagonal, and octagonal.

11. The female sexual simulation device in accordance with claim 9, further comprising: the stimulation mechanisms on the front face of the flexible section are selected from the group consisting of a multiplicity of randomly spaced generally round bumps and a decorative design.

12. The female sexual stimulation device in accordance with claim 9, further comprising the device can be contorted, twisted and bent to form a shape selected from the group consisting of generally tubular shaped, a question mark and an angular shape where the second section is at any desired angle relative to the interconnecting section.

13. The female sexual stimulation device in accordance with claim 9, further comprising: the first section, flexible interconnecting section, and second section are made out of material selected from the group consisting of: soft rubber and sililcone.

14. A female sexual stimulation device, comprising:

a. a first section, a second section, a flexible interconnecting section all formed in one piece, a proximal end of the first section adjoining a first end of the interconnecting section and a proximal end of the second section adjoining a second end of the flexible interconnecting section;

b. the first section having an exterior surface by which the device is grasped by a hand;

c. an activation mechanism retained with the first section and connected to an internal vibration mechanism within the first section, the vibration mechanism connected to a vibration transmitting mechanism extending from the vibration mechanism through an interior of the device and extending through the flexible interconnecting section and into the second section so that when the activation mechanism is activated, the vibration mechanism is activated and causes the vibration transmitting mechanism to vibrate within the device, thereby causing at least the second section to vibrate;

d. the second section having an exterior surface having an interior face and an exterior face, the interior face having a multiplicity of stimulation mechanisms protruding from the interior face, the distal end of the second section is rounded and extends in an arcuate manner relative to interior face projecting away from interior face and having an interior rounded tip, a lubricant reservoir incorporate into the exterior face; and e. the flexible interconnecting section and second section enable the device to be configured, twisted and bent into any desired multiplicity of shapes.

15. The female sexual stimulation device in accordance with claim 14, further comprising the device can be contorted, twisted and bent to form a shape selected from the group consisting of generally tubular shaped, a question mark and an angular shape where the second section is at any desired angle relative to the interconnecting section.

16. A female sexual stimulation device, comprising:

a. a first section, a second section, a flexible interconnecting section all formed in one piece, a proximal end of the first section adjoining a first end of the interconnecting section and a proximal end of the second section adjoining a second end of the flexible interconnecting section;

b. the first section having an exterior surface by which the device is grasped by a hand;

c. an activation mechanism retained with the first section and connected to an internal vibration means which causes at least the second section to vibrate when the vibration means is activated by the activation mechanism;

d. the second section having an exterior surface having a lubricant reservoir incorporate into the exterior surface; and e. the flexible interconnecting section and second section enable the device to be configured, twisted and bent into any desired multiplicity of shapes.

17. The female sexual stimulation device in accordance with claim 16, further comprising: the second section having an exterior surface having an interior face and an exterior face, the interior face having a multiplicity of stimulation mechanisms protruding from the interior face, the distal end of the second section is rounded and extends in an arcuate manner relative to interior face projecting away from interior face and having an interior rounded tip, and the lubricant reservoir incorporated into the exterior face.

18. The female sexual stimulation device in accordance with claim 16, further comprising the device can be contorted, twisted and bent to form a shape selected from the group consisting of generally tubular shaped, a question mark and an angular shape where the second section is at any desired angle relative to the interconnecting section.

* * * * *